(12) United States Patent
McGuinness et al.

(10) Patent No.: US 8,134,038 B2
(45) Date of Patent: Mar. 13, 2012

(54) OLIGOMERISATION OF OLEFINIC COMPOUNDS IN THE PRESENCE OF AN OLIGOMERISATION CATALYST, AND A CATALYST ACTIVATOR INCLUDING A HALOGENATED ORGANIC GROUP

(75) Inventors: David Shane McGuinness, Tasmania (AU); Adam John Rucklidge, Manchester (GB)

(73) Assignee: Sasol Technology (PTY) Limited, Johannesburg (ZA)

(*) Notice: Subject to any disclaimer, the term of this patent is extended or adjusted under 35 U.S.C. 154(b) by 279 days.

(21) Appl. No.: 11/992,740

(22) PCT Filed: Sep. 26, 2006

(86) PCT No.: PCT/IB2006/053494
§ 371 (c)(1),
(2), (4) Date: Apr. 17, 2009

(87) PCT Pub. No.: WO2007/039851
PCT Pub. Date: Apr. 12, 2007

(65) Prior Publication Data
US 2009/0209713 A1    Aug. 20, 2009

(30) Foreign Application Priority Data
Oct. 3, 2005   (GB) .................................. 0520085.2

(51) Int. Cl.
C07C 2/24   (2006.01)
C07C 2/04   (2006.01)
C07C 2/34   (2006.01)

(52) U.S. Cl. .......................... 585/512; 585/510; 585/511

(58) Field of Classification Search .................... 526/154
See application file for complete search history.

(56) References Cited

U.S. PATENT DOCUMENTS

| 3,477,999 | A | 11/1969 | Takeda et al. |
| 5,731,487 | A | 3/1998 | Tamura et al. |
| 2002/0077431 | A1 | 6/2002 | Whiteker |

FOREIGN PATENT DOCUMENTS

| DE | 1 167 833 B | 4/1964 |
| DE | 199 17 984 A1 | 11/2000 |
| DE | 103 56 768 A1 | 7/2005 |
| GB | 1 260 196 | 1/1972 |
| GB | 2 314 518 A | 1/1998 |
| JP | 10 287690 A | 10/1998 |
| JP | 10 316695 A | 12/1998 |
| WO | WO 00/53611 | 9/2000 |
| WO | WO 00/583319 | 10/2000 |
| WO | WO 01/47635 A2 | 7/2001 |
| WO | WO 01/83447 A2 | 11/2001 |
| WO | WO 03/053890 A1 | 7/2003 |
| WO | WO 2004/056479 A1 | 7/2004 |
| WO | WO 2004/056480 A1 | 7/2004 |
| WO | WO 2005/103099 A1 | 11/2005 |

OTHER PUBLICATIONS

Bollmann et al., "Ethylene Tetramerization: A New Route to Produce 1-Octene in Exceptionally High Selectivities," Journal of the American Chemical Society, vol. 126, (2004), pp. 14712-14713.

Britovsek et al., "Oligomerisation of Ethylene by Bis(imino)pyridyliron and -cobalt Complexes," Chemistry—a European Journal, vol. 6, No. 12, (2000), pp. 2221-2231.
Dixon et al., "Advances in selective ethylene trimerisation—a critical overview," Journal of Organometallic Chemistry, vol. 689, (2004), pp. 3641-3668.
Klosin et al., "Ligand Exchange and Alkyl Abstraction Involving (Perfluoroaryl)boranes and -alanes with Aluminum and Gallium Alkyls," Organometallics, vol. 19, (Oct. 11, 2000), pp. 4684-4686.
Schnitter et al., "Synthesis and Characterization of (4-Fluorophenyl)amino-Based Amino- and Iminometallanes of Group 13, etc." Organometallics, vol. 16, (1997), pp. 1197-1202.
Weng et al., "A structurally characterized Ni-Al methyl-bridged complex with catalytic ethylene oligomerization activity," Chemical Communications, (2006), pp. 1319-1321.
Chen et al., "Cocatalysts for Metal-Catalyzed Olefin Polymerization: Activators, Activation Processes, and Structure-Activity Relationships," Chemical Reviews, vol. 100, (2000), pp. 1391-1434.
Barbarich et al., "Coordination of the new weakly coordinating anions $Al(OCH(CF_3)_2)_4^-$, $Al(OC(CH_3)(CF_3)_2)_4^-$, and $Al(OC(PH)(CF_3)_2)_4^-$ to the monovalent metal ions $Li^+$ and $Tl^+$," Journal of Molecular Catalysis A: Chemical vol. 128, (1998), pp. 289-331.
Britovsek et al., "From $B(C_6F_5)_3$ to $B(OC_6F_5)_3$: Synthesis of $(C_6F_5)_2BOC_6F_5$ and $C_6F_5B(OC_6F_5)_2$ and Their Relative Lewis Acidity," Organometallics, vol. 24, (2005), pp. 1685-1691.
Krossing et al., "Noncoodinating Anions-Fact or Fiction? A survey of Likely Candidates," Angewandte Chemie International Edition, vol. 43, No. 16 (2004), pp. 2066-2090.
Krossing et al., "New reagents to introduce weakly coordinating anions of type $Al(OR_F)_4^-$: synthesis, structure and characterization of Cs and trityl salts," Journal of Fluorine Chemistry, vol. 112, (2001), pp. 83-90.
Kaul et al, "Trimethylammonium[tetrakis(pentafluorophenoxy)-borate], a safe way to synthesize novel co-catalysts for olefin polymerization," Journal of Organometallic Chemistry, vol. 621, (2001) pp. 184-189.
Uemura et al., Transformations of Chiral ($\eta^6$-Arene)chromium Complexes in Organic Synthesis: Aldol Reactions of (Ortho-substituted acetophenone)chromium Complexes, Journal of Organic Chemistry, vol. 57, (1992), pp. 5590-5596.
Gregoriades et al., "The Potential of a cyclo-$As_3$-Ligand Complex in Supramolecular Chemistry," Angewandte Chemie International Edition, vol. 45, (2006), pp. 4189-4192.
McGuinness et al., "Cocatalyst Influence in Selective Oligomerization: Effect on Activity, Catalyst Stability, and 1-Hexene/1-Octene Selectivity in the Ethylene Trimerization and Tetramerization Reaction," Organometallics, vol. 26, (2007), 2561-2569.

Primary Examiner — David W Wu
Assistant Examiner — Sonya Wright
(74) Attorney, Agent, or Firm — Finnegan, Henderson, Farabow, Garrett, & Dunner LLP

(57) ABSTRACT

According to the present invention there is provided a process for producing an oligomeric product by the oligomerisation of at least one olefinic compound, by contacting the at least one olefinic compound with the combination of an oligomerisation catalyst and a catalyst activator. The catalyst activator is a compound which includes at least one halogenated organic group which is bound to one or more binding atoms selected from the group consisting of a group 5A atom and a group 6A atom, which one or more binding atoms are in turn bound to a central atom selected from the group consisting of a group 3A atom, and a group 3B to 7B transition metal atom. The oligomerisation catalyst includes the combination of i) a source of a transition metal; and ii) a ligating compound of the formula $(R^1)mX^1(Y)X^2(R^2)n$ The invention also relates to a combination of an aligomerisation catalyst and a catalyst activator as set out above and to the use of such a combination in an oligomerisation process.

16 Claims, 2 Drawing Sheets

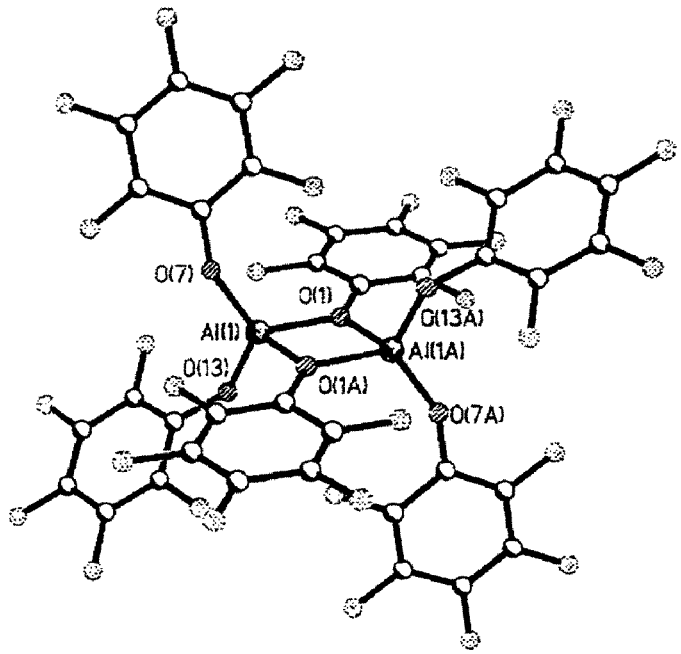
Figure 1. Molecular structure of $\{Al(OC_6F_5)_3\}_2$
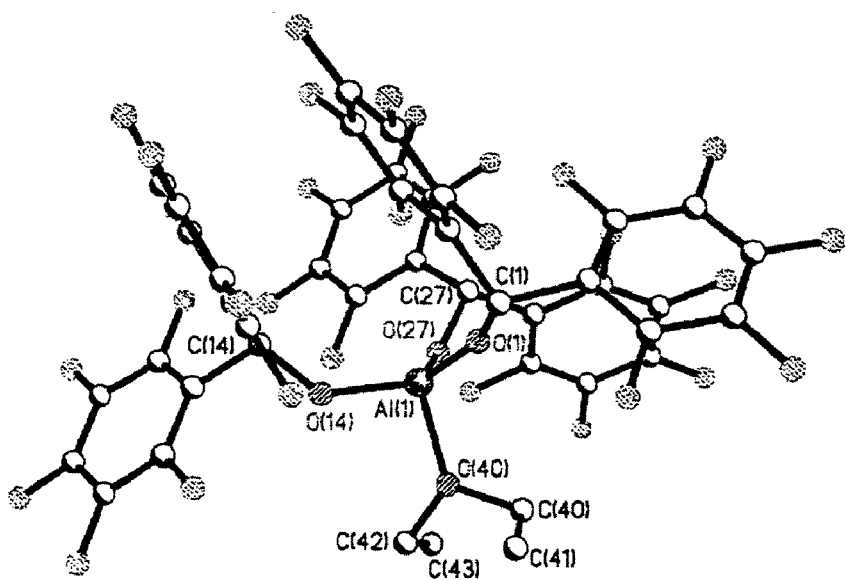
Figure 2. Molecular structure of $(Et_2O)Al[OCH(C_6F_5)_2]_3$

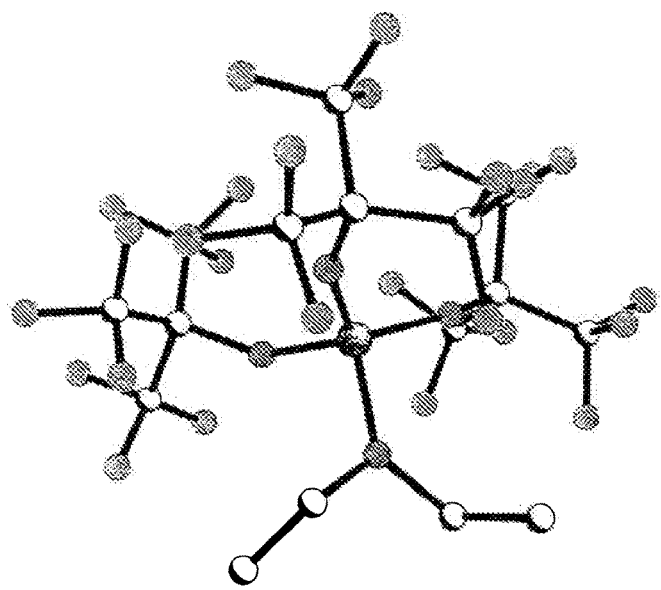
Figure 3. Molecular structure of $(Et_2O)Al[OC(CF_3)_3]_3$
Figure 4. Mass ratio of $C_8$ / $C_6$ as a function of amount of activator
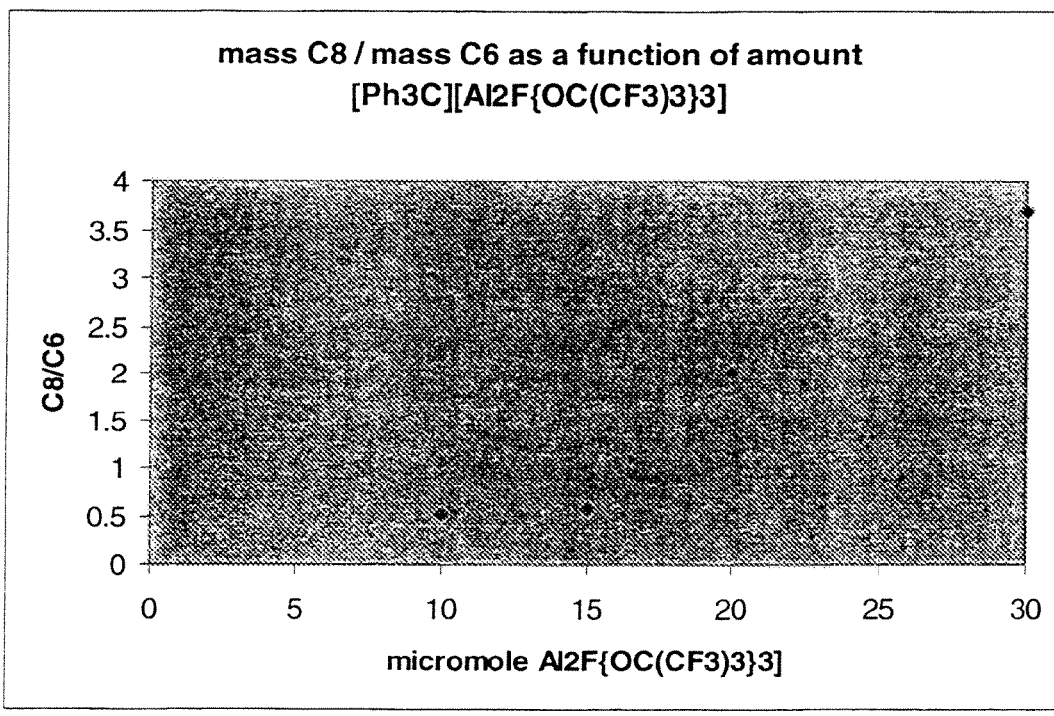

US 8,134,038 B2

OLIGOMERISATION OF OLEFINIC COMPOUNDS IN THE PRESENCE OF AN OLIGOMERISATION CATALYST, AND A CATALYST ACTIVATOR INCLUDING A HALOGENATED ORGANIC GROUP

TECHNICAL FIELD

This invention relates to the oligomerisation of olefinic compounds in the presence of an oligomerisation catalyst, and a catalyst activator including a halogenated organic group.

BACKGROUND ART

A number of different oligomerisation technologies are known to produce α-olefins. Some of these processes, including the Shell Higher Olefins Process and Ziegler-type technologies, have been summarized in WO 04/056479 A1. The same document also discloses that the prior art (e.g. WO 03/053891 and WO 02/04119) teaches that chromium based catalysts containing heteroaromatic ligands with both phosphorus and nitrogen heteroatoms, selectively catalyse the trimerisation of ethylene to 1-hexene.

Processes wherein transition metals and heteroatomic ligands are combined to form catalysts for trimerisation, tetramerisation, oligomerisation and polymerisation of olefinic compounds have also been described in different patent applications such as WO 03/053890 A1; WO 03/053891; WO 04/056479 A1; WO 04/056477 A1; WO 04/056480 A1; WO 04/056478 A1; U.S. Complete patent application Ser. No. 11/130,106; WO 05/123884 A2 and WO 05/123633 A1.

The catalysts utilized in the abovementioned trimerisation, tetramerisation, oligomerisation or polymerisation processes all include one or more catalyst activators to activate the catalyst. Such an activator is a compound that generates an active catalyst when the activator is combined with the catalyst.

Suitable activators include organoaluminium compounds, organoboron compounds, organic salts, such as methyl lithium and methyl magnesium bromide, inorganic acids and salts, such as tetrafluoroboric acid etherate, silver tetrafluoroborate, sodium hexafluoroantimonate and the like.

A common catalyst activator used in combination with Cr based catalysts for oligomerisation of olefinic compounds is alkylaluminoxane, particularly methylaluminoxane (MAO). It is well known that MAO includes significant quantities of alkylaluminium in the form of trimethylaluminium (TMA), and in effect the catalyst activator is a combination of TMA and MAO. The MAO may also be replaced with modified MAO (MMAO).

The use of fluorinated boranes/borates as catalyst activators is also known. In J Organomet. Chem. 683 (2003) 200 triazacyclohexane $CrCl_3$ complexes were activated with $AlR_3$ and $[PhN(Me)_2H]^+[B(C_6F_5)_4]^-$ to give catalysts active for trimerisation of alpha-olefins. In J. Am. Chem. Soc., 126 (2004) 1304, Cr-based ethylene trimerisation catalysts were activated by treating Cr-aryl complexes with fluorinated arylboranes (BARF). IPCOM000031729D discloses the use of fluorinated borate and borane activators in combination with chromium based catalyst in the oligomerisation of olefins.

In WO 99/64476, catalysts (especially Ziegler-Natta and metallocene polymerisation catalysts) were activated by a combination of halogenated aryl containing Group13 metal or metalloid based Lewis acids and organo-Group13 metal compounds.

Trityl tetrakis(pentafluorophenoxo)aluminate, $[Ph_3C]^+[Al(OC_6F_5)_4]^-$, has been prepared and employed as a co-catalyst for ethylene and propylene polymerisation with metallocene complexes such as $(C_5H_5)_2ZrMe_2$ in Organometallics, 19 (2000) 1625 and Organometallics, 21 (2002) 3691. Angew. Chem. Int. Ed. 2004, 43, 2066 also discloses compounds such as $[M(OC_6F_5)_n]$ and $[Al\{OC(CF_3)_3\}_4]^-$ and the use of the latter as an activator for ethene and propene polymerisation with a Zr-alkyl complex in the presence of $Al_iBu_3$. J. Fluorine Chemistry 2001, 112, 83 discloses the preparation of compounds such as $[Ph_3C]^+[Al\{OC(CF_3)_3\}_4]^-$.

Journal of Organometallic Chemistry, 621 (2001), 184 discloses the use of $[Me_3NH]^+[B(OC_6F_5)_4]^-$ for polymerisation with iron catalysts including tridentate ligands.

It has now been found that compounds of the present invention including at least one halogenated organic group bound to a group 3A or group 3B to 7B central atom by means of one or more binding atoms can be used as activators of oligomerisation catalysts in oligomerisation reactions. In some cases the productivity of the oligomerisation catalysts was found to have been improved compared to when borane or borate activators are used, such as those detailed in IPCOM000031729D. Most surprisingly it also has been found that different activators of this nature can influence the product selectivity of the oligomerisation catalysts. Furthermore, the relative high polymer formation associated with borate activators, was at least reduced in at least some cases.

BRIEF DESCRIPTION OF THE DRAWINGS

FIG. 1 is the molecular structure of $\{Al(OC_6F_5)_3\}_2$.
FIG. 2 is the molecular structure of $(Et_2O)Al[OCH(C_6F_5)_2]_3$.
FIG. 3 is the molecular structure of $(Et_2O)Al[OC(CF_3)_3]_3$.
FIG. 4 is the mass ratio of $C_8/C_6$ as a function of amount of activator of Examples 34-37.

DISCLOSURE OF THE INVENTION

According to the present invention there is provided a process for producing an oligomeric product by the oligomerisation of at least one olefinic compound in the form of an olefin or a compound including a carbon to carbon double bond, by contacting the at least one olefinic compound with the combination of an oligomerisation catalyst and a catalyst activator, which catalyst activator is a compound which includes at least one halogenated organic group which is bound to one or more binding atoms selected from the group consisting of a group 5A atom and a group 6A atom, which one or more binding atoms are in turn bound to a central atom selected from the group consisting of a group 3A atom, and a group 3B to 7B transition metal atom; and wherein the oligomerisation catalyst includes the combination of
i) a source of a transition metal; and
ii) a ligating compound of the formula

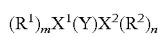

wherein:
X$^1$ and X$^2$ are independently selected from the group consisting of N, P, As, Sb, Bi, O, S and Se;
Y is a linking group between X$^1$ and X$^2$;
m and n are independently 0, 1 or a larger integer; and
R$^1$ and R$^2$ are independently hydrogen, a hydrocarbyl group or a heterohydrocarbyl group, and R$^1$ being the same or different when m>1, and R$^2$ being the same or different when n>1.

In this specification a heterohydrocarbyl group is a univalent or multivalent organic compound which includes at least one heteroatom (that is not being H or C), and which organic compound binds with one or more other moieties through one or more carbon atoms of the organic compound and/or one or more heteroatoms of the organic compound. Organoheteryl groups and organyl groups (which include at least one heteroatom) are examples of heterohydrocarbyl groups.

In this specification a hydrocarbyl group is a univalent or multivalent group formed by removing one or more hydrogen atoms from a hydrocarbon.

Accordingly to another aspect of the present invention there is provided the use of a combination of a catalyst activator and an oligomerisation catalyst in the oligomerisation of at least one olefinic compound in the form of an olefin or a compound including a carbon to carbon double bond by contacting the at least one olefinic compound with the oligomerisation catalyst, and the catalyst activator, wherein the activator is a compound which includes at least one halogenated organic group which is bound to one or more binding atoms selected from the group consisting of a group 5A atom and a group 6A atom, which one or more binding atoms are in turn bound to a central atom selected from the group consisting of a group 3A atom, and a group 3B to 7B transition metal atom; and wherein oligomerisation catalyst includes a combination of
i) a source of a transition metal; and
ii) a ligating compound of the formula

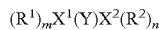

wherein:
X$^1$ and X$^2$ are independently selected from the group consisting of N, P, As, Sb, Bi, O, S and Se;
Y is a linking group between X$^1$ and X$^2$;
m and n are independently 0, 1 or a larger integer; and
R$^1$ and R$^2$ are independently hydrogen, a hydrocarbyl group or a heterohydrocarbyl group, and R$^1$ being the same or different when m>1, and R$^2$ being the same or different when n>1.

It has been found that the activator often provides good activity and even improved productivity compared to boranes and borates. Polymer formation has also been reduced in at least some cases. In comparison to the use of aluminoxanes as activator, the amount of activator required relative to catalyst has been reduced in most cases. This has led to lower waste volumes (such as lower aluminium oxide in the product) and reduced activator cost. It has also been found that the activator influences the product selectivity specifically in respect of the molar ratio of trimer tetramer formed.

Combination of Catalyst and Activator

The catalyst and activator may be combined prior to being contacted with the olefinic compound. The catalyst and activator may react with each other to form a reaction product of the catalyst and the activator. The activator and catalyst may form part of the same compound. The said reaction product may be an ionic reaction product.

Activator

Preferably the activator is a Lewis acid.

As stated above the one or more binding atoms are bound to a central atom selected from the group consisting a group 3A atom, and a group 3B to 7B transition metal atom. The central transition metal atom is preferably selected from the group consisting of Nb, Ta, Y and La. Preferably the transition metal atom is Ta. Preferably the one or more binding atoms are bound to a central group 3A atom. Preferably the central group 3A atom is selected from the group consisting of Al and B, preferably it is Al.

The or each binding atom is preferably an atom selected from the group consisting of O, N, P and S. Preferably it is O.

In one embodiment of the invention the activator may include only one or more halogenated organic groups bound to one or more binding atoms as set out above, which one or more binding atoms are groups bound to the central atom as set out above. In an alternative embodiment of the invention the activator may also include one or more atoms or groups of atoms other than said one or more halogenated organic groups bound to said one or more binding atoms.

The at least one halogenated organic group may be bound to each binding atom by means of a carbon atom and/or a non-carbon atom. The halogenated organic group may be a halogenated hydrocarbyl group or a halogenated heterohydrocarbyl group. The halogenated organic group may be a halogenated organyl group or a halogenated organoheteryl group. Preferably it is a halogenated hydrocarbyl group.

In one embodiment of the invention the activator may be a compound of the formula, or the activator may include a moiety of the formula

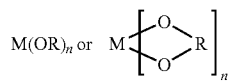

wherein
M is selected from the group consisting of a group 3A atom, and a group 3B to 7B transition metal atom;
n is 1 or a larger integer; and
R is a halogenated organic group, R being the same or different when n is larger than 1.

The group 3B to 7B transition metal atom is preferably selected from the group consisting of Nb, Ta, Y and La. Preferably it is Ta. Preferably M is a group 3A atom. Preferably the group 3A atom is selected from the group consisting of Al and B, preferably it is Al.

R may be bound to each O by means of a carbon atom and/or a non-carbon atom. R may be a halogenated hydrocarbyl group, or a halogenated heterohydrocarbyl group or a halogenated organyl group, or a halogenated organoheteryl group.

In one embodiment of the invention the activator may be a compound of the formula

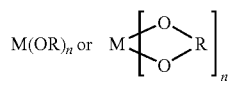

wherein M, R and n are as defined above. Alternatively the activator may be a compound which includes a moiety of the formula

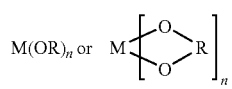

wherein M, R and n are as defined above, and M is bound to at least one moiety Z which is not a

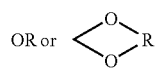

group as defined above. Preferably Z is a halide or a hydrocarbyl group or heterohydrocarbyl group. Preferably Z is a halide or an organoheteryl group. Preferably Z is —O(R$^{10}$)$_2$ wherein R$^{10}$ is a hydrocarbyl group, and R$^{10}$ being the same or different. $R^{10}$ may be alkyl and preferably it is ethyl. Alternatively Z may be halide, preferably in the form of F. Alternatively, the activator may be a salt containing an anion which includes a moiety of the formula

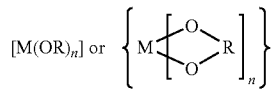

preferably the anion is

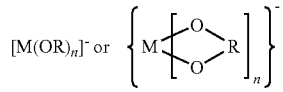

wherein M, R and n are as defined above.

Preferably R is a halogenated hydrocarbyl group or a halogenated organyl group. The halogenated organyl group or halogenated hydrocarbyl group may comprise an organyl group or hydrocarbyl group wherein at least one hydrogen atom has been replaced with a halogen atom. Preferably all the hydrogen atoms of the organyl group or hydrocarbyl group are replaced with halogen atoms. Preferably all the halogen atoms are the same. Preferably the halogen atom is F.

The halogenated organic group may be a monovalent or divalent halogenated hydrocarbyl group in the form of a hydrocarbyl group wherein at least one hydrogen atom has been replaced with a halogen atom. Preferably all the hydrogen atoms of the hydrocarbyl group are replaced with halogen atoms. Preferably all the halogen atoms are the same. Preferably the halogen atom is F. The halogenated hydrocarbyl group may comprise a halogenated acylic hydrocarbyl group or a halogenated cyclic hydrocarbyl group. The halogenated acyclic hydrocarbyl group may comprise a halogenated alkyl, preferably a halogenated branched alkyl, preferably halogenated isobutyl or tertiary-butyl. The halogenated cyclic hydrocarbyl group may comprise a halogenated aromatic compound, preferably a halogenated phenyl group.

In one embodiment of the invention the activator may be selected from the group consisting of a compound $Al(OR)_3$, a salt containing the anion

a compound including a moiety $Al(OR)_3$ and a salt containing the anion $[Ta(OR)_6]^-$ wherein R is defined as above.

In one embodiment of the invention the activator may be selected from the group consisting of $Al(OC_6F_5)_3$; $X^+[Al\{OC(CF_3)_3\}_4]^-$; $X^+[Al(OC_6F_5)_4]^-$; $X^+[Al(C_6F_4O_2)_2]^-$; $X^+[Al\{OC(CF_3)_2C(CF_3)_2O\}_2]^-$; $X^+[AlF\{OC(CF_3)_3\}_3]$; $X^+[Al_2F\{OC(CF_3)_3\}_6]$; $(Z)Al\{OCH(C_6F_5)_2\}_3$; $(Z)Al\{OC(CF_3)_3\}_3$ and $X^+[Ta(OC_6F_5)_6]^-$ wherein $X^+$ is a cation including $Ph_3C^+$, $Me_2PhNH^+$ and $(Et_2O)_2H^+$; and wherein Z is a moiety bound to Al which moiety Z is not an (OR) group or

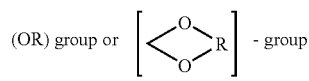

where R is a halogenated organic group.

The amount of activator used may be between 1-100 equivalents relative to the catalyst transition metal. Preferably it is less than 5 equivalents relative to the catalyst transition metal, and most preferably between 1-3 equivalents relative to the catalyst transition metal.

The activator may be prepared in situ, alternatively it may be preformed. In one embodiment of the invention the activator may be preformed from the co-activator as described herein below.

Co-Activator

The process may also include a co-activator which is a compound not falling within the definition of the activator. Preferably the co-activator includes no halogenated organic group which is bound to one or more binding atoms selected from the group consisting of a group 5A atom and a group 6A atom, which one or more binding atoms are in turn bound to a central atom selected from the group consisting of a group 3A atom, and a group 3B to 7B transition metal atom. Preferably the co-activator is a compound which includes at least one moiety selected from the group consisting of an organic group (preferably an organyl group), a halogenated organic group (preferably a halogenated organyl group) and hydrogen; and the moiety being bound to an atom selected from the group consisting of a group 3A atom, a group 4A atom, and a metal atom, including an alkali metal atom and an alkaline earth metal atom.

Preferably the co-activator as set out above is an organoaluminium compound and/or an organoboron compound. Alternatively it may be an organic salt such as methyl lithium and/or methyl magnesium bromide.

Examples of suitable organoboron compounds are boroxines, triethylborane, tris(pentafluorophenyl)borane, tributyl borane and the like.

Suitable organoaluminium compounds include compounds of the formula $Al(R^9)_3$ ($R^9$ being the same or different), where each $R^9$ is independently an organyl group, a halogenated organyl group or a halide, with at least one of $R^9$ being an organyl group or a halogenated organyl group. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes.

Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

The co-activator may comprise a compound of the formula $M'(R')_n$.

wherein
  M' is selected from the group consisting of a group 3A atom, a group 4A atom and a metal atom, including an alkali metal atom and an alkaline earth metal atom;
  n is 1 or a larger integer; and
  R' is an organic group, R' being the same or different when n is larger than 1.

Preferably M' is selected from the group consisting of a group 3A atom, a group 4A atom, and a transition metal atom. Preferably the R group is bound to a group 3A atom. Preferably the group 3A atom is selected from the group consisting of Al and B, preferably it is Al.

The organic group R may be an organyl group, and preferably it comprises a hydrocarbyl group, preferably it comprises an alkyl group, preferably methyl, ethyl or a larger alkyl group.

In one embodiment of the invention the co-activator comprises $AlR''_3$ wherein R" is an alkyl group.

The co-catalyst may be selected from the group consisting of trimethylaluminium (TMA); triethylaluminium (TEA), tributylaluminium, tri-isobutylaluminium (TIBA) and tri-n-octylaluminium.

It will be appreciated that TMA is relatively expensive and accordingly the use thereof may be wished to be avoided. It has been found that by using an activator as defined in the present invention in combination with a co-activator as defined above (but excluding TMA and MAO) the use of TMA can be avoided as a co-catalyst.

It is foreseen that a co-activator as defined hereinabove will usually be used in combination with an activator as defined above. However, it may be possible, by selecting a suitable source of transition metal (i) and/or a ligating compound (II), that the use of the co-activator may be avoided. It is believed (without being bound thereto) that a co-activator such as TMA is used to alkylate the catalyst formed by the combination of (i) and (ii) and that the activator then acts on alkyl abstracting agent of the alkylated catalyst to activate the said catalyst.

The amount of co-activator employed may be up to 1000 equivalents relative to the transition metal catalyst, but preferable is less than 600 equivalents. Preferably it is in the range between 30-300 equivalents relative to the transition metal catalyst.

In use where both an activator and a co-activator are used, the co-activator may be added first and the activator may be added subsequently.

Oligomeric Product

The oligomeric product may be an olefin, or a compound including an olefinic moiety. Preferably the oligomeric product includes an olefin, more preferably an olefin containing a single carbon-carbon double bond, and preferably it includes an α-olefin. The olefin product may include hexene, preferably 1-hexene, alternatively or additionally it includes octene, preferably 1-octene. In a preferred embodiment of the invention the olefinic product includes a mixture of hexene and octene, preferably a mixture of 1-hexene and 1-octene.

In one preferred embodiment of the invention the oligomerisation process is a selective process to produce an oligomeric product containing more than 30% by mass of total product of a single olefin product. The olefin product may be hexene, preferably 1-hexene, but alternatively it may be octene, preferably 1-octene.

Preferably the product contains at least 35% of the said olefin, preferably α-olefin, but it may be more than 40%, 50%, or even 60% by mass.

The olefinic product may be branched, but preferably it is non-branched.

Oligomerisation

The oligomerisation process may comprise a trimerisation process, alternatively or additionally it may comprise a tetramerisation process.

The process may be oligomerisation of two or more different olefinic compounds to produce an oligomer containing the reaction product of the two or more different olefinic compounds. Preferably however, the oligomerisation (preferably trimerisation and/or tetramerisation) comprises the oligomerisation of a single monomer olefinic compound.

In one preferred embodiment of the invention the oligomerisation process is oligomerisation of a single α-olefin to produce an oligomeric α-olefin. Preferably it comprises the trimerisation and/or tetramerisation of ethylene, preferably to 1-hexene and/or 1-octene.

Olefinic Compound to be Oligomerised

The olefinic compound may comprise a single olefinic compound or a mixture of olefinic compounds. In one embodiment of the invention it may comprise a single olefin.

The olefin may include multiple carbon-carbon double bonds, but preferably it comprises a single carbon-carbon double bond. The olefin may comprise an α-olefin with 2 to 30 carbon atoms, preferably 2 to 10 carbon atoms. The olefinic compound may be selected from the group consisting of ethylene, propene, 1-butene, 1-pentene, 1-hexene, 1-heptene, and 1-octene, 1-nonene, 1-decene, 3-methyl-1-butene, 3-methyl-1-pentene, 4-methyl-1-pentene, styrene, p-methyl styrene, 1-dodecene or combinations thereof. Preferably it comprises ethylene or propene, preferably ethylene. The ethylene may be used to produce hexene and/or octene, preferably 1-hexene and/or 1-octene.

Catalyst

Source of Transition Metal (i)

Preferably the source of transition metal as set out in (i) above is a source of a Group 4B to 6B transition metal. Preferably it is a source of Cr, Ti, V, Ta or Zr, more preferably Cr, Ti, V or Ta. Preferably it is a source of either Cr, Ta or Ti. Most preferably it is a source of Cr.

The source of the Group 4B to 6B transition metal may be an inorganic salt, an organic salt, a coordination compound or an organometallic complex.

Preferably the source of transition metal is a source of chromium and preferably it is selected from the group consisting of chromium trichloride tris-tetrahydrofuran; (benzene)tricarbonyl chromium; chromium (III) octanoate; chromium hexacarbonyl; chromium (III) acetylacetonate, chromium (III) naphthenate, chromium (III) 2-ethylhexanoate. Preferably it is chromium trichloride tris-tetrahydrofuran or chromium (III) acetylacetonate.

Ligating Compound $X^1$ and/or $X^2$ may be a potential electron donor for coordination with the transition metal referred to in (i).

An electron donor is defined as an entity that donates electrons used in chemical, including dative covalent, bond formation.

$X^1$ and/or $X^2$, may be independently oxidised by S, Se, N or O.

$X^1$ and/or $X^2$ may be independently phosphorus or phosphorus oxidised by S, Se, N or O. Preferably $X^1$ and $X^2$ are the same, and preferably both are P.

It will be appreciated that m and n are dependent on factors such as the valence and oxidation state of $X^1$ and $X^2$, bond formation of Y with $X^1$ and $X^2$ respectively, and bond formation of $R^1$ and $R^2$ with $X^1$ and $X^2$ respectively. Preferably both m an n are not 0.

Preferably the ligating compound is a bidentate or tridentate ligand, preferably a bidentate ligand.

Preferably the ligating compound is of the formula

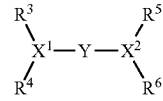

wherein Y is as defined above; $X^1$ and $X^2$ are independently selected from the group consisting of N, P, As, Sb and Bi; and $R^3$ to $R^6$ are each independently a hydrocarbyl group or a heterohydrocarbyl group.

Preferably $X^1$ and $X^2$ are independently selected from the group consisting of P, S and N. Preferably $X^1$ and $X^2$ are the same. Preferably both $X^1$ and $X^2$ are P.

One or more of $R^3$ to $R^6$ may be a substituted hydrocarbyl group or a substituted heterohydrocarbyl group, that is at least one substituent is bound to the hydrocarbyl group or the heterohydrocarbyl group. In this specification a substituent with reference to compounds bound to $X^1$ and/or $X^2$ is a moiety (excluding H) which is bound to a linear structure or a cyclic structure bound to $X^1$ and/or $X^2$, but the substituent does not form part of the linear or cyclic structure. The linear or cyclic structure may be selected from the group consisting of a linear hydrocarbyl, a cyclic hydrocarbyl and a cyclic heterohydrocarbyl group. Linear hydrocarbyl may include ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl. Cyclic hydrocarbyl may include cyclopropyl, cyclobutyl, cyclopentyl, cyclohexyl, cycloheptyl, cyclooctyl, cyclononyl, cyclodecyl, cyclopentenyl, cyclohexenyl, cyclo-octenyl, phenyl, cyclopentadienyl, naphthaleneyl, norbornyl, adamantyl, phenanthreneyl, anthraceneyl, phenaleneyl, tetrahydronaphthaleneyl, decalinyl, indenyl and tetrahydroindenyl. Cyclic heterohydrocarbyl may include tetrahydrofuranyl, tetrahydrothiopheneyl, pyrrolideneyl, piperidineyl, pyrrolineyl, oxazolyl, thiazolyl, furanyl, thiopheneyl, pyrazolinyl, pyrazolyl, imidazolyl, benzofuranyl, coumaranyl and indolyl.

$R^3$ to $R^6$ may also be selected from a group of metallocenes such as a ferroceneyl, zirconoceneyl and titanoceneyl group.

Preferably none of $R^3$ to $R^6$ are aromatic with a ring atom of the aromatic ring structure bound to either $X^1$ or $X^2$ and with a polar substituent as a non-ring atom bound to a ring atom of the aromatic ring structure adjacent to the ring atom bound to $X^1$ or $X^2$.

In this specification a polar substituent is a substituent with a permanent electric or induced dipole moment.

Preferably, if two or more of $R^3$ to $R^6$ are aromatic with a ring atom of the aromatic ring structure bound to either $X^1$ and $X^2$ not more than two of said aromatic $R^3$ to $R^6$ have a substituent as a non-ring atom bound to a ring atom of the aromatic ring structure adjacent to the ring atom bound to $X^1$ or $X^2$.

In one embodiment of the invention $R^3$ to $R^6$ are the same or different and each is a hydrocarbyl group, or a heterohydrocarbyl group which contains no substituent or contains a non-polar substituent. Preferably each of $R^3$ to $R^6$ does not have any polar substituent. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a non-polar substituent other than H as a non-ring atom bound to a ring atom of the aromatic ring structure adjacent to the ring atom bound to $X^1$ or $X^2$. Preferably none of the aromatic $R^3$ to $R^6$ have a non-polar substituent as a non-ring atom bound to a ring atom of the aromatic ring structure adjacent to the ring atom bound to $X^1$ or $X^2$. Preferably all of aromatic $R^3$ to $R^6$ are non-substituted aromatic compounds. $R^3$ to $R^6$ may be independently selected from the group consisting of a non-aromatic compound; an aromatic compound; and a heteroaromatic compound. Preferably each of $R^3$ to $R^6$ is an aromatic or heteroaromatic compound, more preferably an aromatic compound (including a substituted aromatic compound). The aromatic compound (or substituted aromatic compound) may comprise phenyl or a substituted phenyl.

In this specification a non-polar substituent is a substituent without a permanent electric or induced dipole moment.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^5$ may be independently linked to one or more of each other, or to Y to form a cyclic structure.

$R^3$ and $R^4$ may be the same and $R^5$ and $R^6$ may be the same. $R^3$ to $R^6$ may all be the same.

In another embodiment of the invention $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more or all of $R^3$ to $R^6$ may be independently selected from the group consisting of a substituted non-aromatic compound; a substituted aromatic compound; and a substituted heteroaromatic compound. Preferably each of $R^3$ to $R^6$ is a substituted aromatic or a substituted heteroaromatic compound, more preferably a substituted aromatic compound. The substituted aromatic compound may comprise a substituted phenyl. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a substituent as a non-ring atom bound to a ring atom of the aromatic ring structure adjacent to the ring atom bound to $X^1$ or $X^2$.

Any polar substituent on one or more of $R^3$, $R^4$, $R^5$ and $R^6$ may be electron donating. Suitable polar substituents may be a methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, pentafluorophenoxy, tosyl, methylsulfanyl, trimethylsiloxy, dimethylamino, sulphate, nitro, halides or the like.

Y may be selected from the group consisting of an organic linking group such as a hydrocarbyl, substituted hydrocarbyl, heterohydrocarbyl and a substituted heterohydrocarbyl; an inorganic linking group such as a single atom link (that is $X^1$ and $X^2$ are bound to the same atom); methylene; dimethylmethylene; 1,2-ethane; 1,2-ethene; 1,1-cyclopropane; 1,1-cyclobutane; 1,1-cyclohexane; 1,1-cyclopentane; 1,2-cyclopentane; 1,2-cyclohexane; 1,2-phenylene; 1,8-naphthyl; 9,10-phenanthrene; 4,5-phenanthrene; 1,3-propane; 1,2-catechol, 1,2-diarylhydrazine and 1,2-dialkylhydrazine; —B($R^7$)—, —Si($R^7$)$_2$—, —P($R^7$)— and —N($R^7$)— where $R^7$ is hydrogen, a hydrocarbyl or heterohydrocarbyl or halogen. Preferably, Y may be —N($R^7$)— and $R^7$ may be selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof, and aryl substituted with any of these substituents. Preferably $R^7$ may be a hydrocarbyl or a heterohydrocarbyl group. $R^7$ may be methyl, ethyl, propyl, isopropyl, cyclopropyl, allyl, butyl, tertiary-butyl, sec-butyl, cyclobutyl, pentyl, isopentyl, neopentyl, cyclopentyl, cyclohexyl, cycloheptyl, cyclo-octyl, decyl, cyclodecyl, 1,5-dimethylheptyl, 2-naphthylethyl, 1-naphthylmethyl, adamantylmethyl, adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, isopinocamphenyl, dimethylamino, phthalimido, pyrrolyl, trimethylsilyl, dimethyl-tertiary-butylsilyl, 3-trimethoxysilane-propyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, 1,2,3,4-tetrahydronaphthyl, or a 2-octyl group.

In one embodiment of the invention Y may exclude $(CH_2)_x Z(CH_2)_y$, where Z is —$P(R^8)$—, —$N(R^8)$—, —$As(R^8)$—, —$Sb(R^8)$— or —S— and x and y are individually 1-15 and wherein $R^8$ is hydrogen or a halogen or a nitro group or a hydrocarbyl or a substituted hydrocarbyl group.

In another embodiment of the invention Y includes no heteroatom (that is an atom other than H or C) as a ring member of a heteroaromatic ring structure in the shortest link of Y between $X^1$ and $X^2$. Y may include at least one heteroatom (that is neither H or C) in the shortest link of Y between $X^1$ and $X^2$ and preferably said heteroatom is different to $X^1$ and $X^2$. Preferably $X^1$ and $X^2$ are the same and said heteroatom is different to $X^1$ and $X^2$, preferably said heteroatom is N.

Y may include a first atom bound to $X^1$ and a different atom bound to $X^2$, such as the case where Y is 1,2 ethane. Preferably Y includes or is a single atom bound to both $X^1$ and $X^2$.

Preferably the ligating compound is of the formula

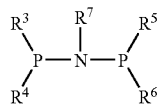

with $R^3$ to $R^7$ as defined above.

Preferably each of $R^3$ to $R^6$ is an alkyl (preferably methyl, ethyl or isopropyl) or aromatic (preferably phenyl or substituted phenyl).

Non limiting examples of the ligating compound are (phenyl)$_2$PN(propyl)P(phenyl)$_2$; (phenyl)$_2$PN(cyclopentyl)P(phenyl)$_2$; (phenyl)$_2$PN(isopropyl)P(phenyl)$_2$; (phenyl)$_2$PN((4-t-butyl)-phenyl)P(phenyl)$_2$; (2-naphthyl)$_2$PN(methyl)P(phenyl)$_2$; (2-methylphenyl)(phenyl)PN(isopropyl)P(2-methylphenyl)(phenyl); (ethyl)(phenyl)P-1,2-benzene-P(ethyl)(phenyl); (4-methoxyphenyl)$_2$PN(isopropyl)P(phenyl)$_2$; (2-methoxyphenyl)$_2$P-1,2-benzene-P(2-methoxyphenyl)$_2$;

The ligating compound may include a polymeric moiety to render the reaction product of the source of transition metal and the said ligating compound to be soluble at higher temperatures and insoluble at lower temperatures e.g. 25° C. This approach may enable the recovery of the complex from the reaction mixture for re-use and has been used for other catalyst as described by D. E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone as, for example, demonstrated by C. Yuanyin et al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p methoxyphenyl)$_2$)-benzene.

The ligating compounds may be prepared using procedures known to one skilled in the art and procedures forming part of the state of the art.

The oligomerisation catalyst may be prepared in situ, that is in the reaction mixture in which the oligomerisation reaction is to take place. Often the oligomerisation catalyst will be prepared in situ. Alternatively the catalyst may be pre-formed or partly pre-formed.

The source of transition metal and ligating compound may be combined (in situ or ex situ) to provide any suitable molar ratio, preferably a transition metal to ligand compound molar ratio, from about 0.01:100 to 10 000:1, preferably from about 0.1:1 to 10:1.

The process may also include combining one or more different sources of transition metal with one or more different ligating compounds.

The oligomerisation catalyst or its individual components, in accordance with the invention, may also be immobilised by supporting it on a support material, for example, silica, alumina, MgCl$_2$, zirconia, artificial hectorite or smectite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

Process

The olefinic compound or mixture thereof to be oligomerised according to this invention can be introduced into the process in a continuous or batch fashion.

The olefinic compound or mixture of olefinic compounds may be contacted with the catalysts at a pressure of 1 barg or higher, preferably greater than 10 barg (1000 kPa), more preferably greater than 30 barg (3000 kPa). Preferred pressure ranges are from 10 to 300 barg (1000 to 3000 kPa), more preferably from 30 to 100 barg (3000 to 10000 kPa).

The process may be carried out at temperatures from −100° C. to 250° C. Temperatures in the range of 15-150° C. are preferred. Particularly preferred temperatures range from 35-120° C.

The reaction products derived from the reaction as described herein, may be prepared using the disclosed catalysts by a homogeneous liquid phase reaction in the presence or absence of an inert solvent, and/or by slurry reaction where the catalysts and the oligomeric product is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The reaction may also be carried out in an inert solvent. Any inert solvent that does not react with the activator can be used. These inert solvents may include any saturated aliphatic and unsaturated aliphatic and aromatic hydrocarbon and halogenated hydrocarbon. Typical solvents include, but are not limited to, benzene, toluene, xylene, cumene, heptane, methylcyclohexane, methylcyclopentane, cyclohexane, ionic liquids as well as the product formed during the reaction in a liquid state and the like.

The reaction may be carried out in a plant which includes reactor types known in the art. Examples of such reactors include, but are not limited to, batch reactors, semi-batch reactors and continuous reactors. The plant may include, in combination a) a stirred or fluidised bed reactor system, b) at least one inlet line into this reactor for olefin reactant and the catalyst system, c) effluent lines from this reactor for oligomerisation reaction products, and d) at least one separator to separate the desired oligomerisation reaction products which may include a recycle loop for solvents and/or reactants and/or products which may also serve as temperature control mechanism.

According to another aspect of the present invention there is provided an oligomerisation product prepared by a process substantially as described hereinabove.

According to another aspect of the present invention there is provided the combination of an oligomerisation catalyst and a catalyst activator, which catalyst activator is a compound which includes at least one halogenated organic group which is bound to one or more binding atoms selected from the group consisting of a group 5A atom and a group 6A atom, which one or more binding atoms are in turn bound to a central atom selected from the group consisting of a group 3A atom, and a group 3B to 7B transition metal atom; and wherein the oligomerisation catalyst includes the combination of iii) a source of a transition metal; and
iv) a ligating compound of the formula $(R^1)_m X^1(Y)X^2(R^2)_n$ wherein:
$X^1$ and $X^2$ are independently selected from the group consisting of N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group or a heterohydrocarbyl group, and $R^1$ being the same or different when m>1, and $R^2$ being the same or different when n>1.

The invention will now be further described by means of the following non-limiting examples.

EXAMPLES

In the examples that follow, all manipulations were carried out under inert conditions, using standard Schlenk techniques. All solvents were dried and degassed via normal procedures. [Ph$_3$C][Al{OC(CF$_3$)$_3$}$_4$] was prepared following the method described by Krossing et. al., Journal of Fluorine Chemistry, 112 (2001), 83-90. The ethylene used in the catalyst testing was supplied by BOC and was grade 3.0 unless otherwise stated.

Example 1

Preparation of {Al(OC$_6$F$_5$)$_3$}$_2$

A solution of 2M perfluorophenol (7.0 ml, 14 mmol) in toluene was added to a flask and a 1.9M solution of triethylaluminium (2.0 ml, 3.8 mmol) was added dropwise. The solution was then heated to 60° C. for 4 hours and then allowed to cool. The solvent toluene was reduced under vacuum and 10 ml of petroleum spirits added. The resulting powder that formed was washed four times with petroleum spirits (5 ml) and dried under vacuum to afford a white powder. Yield: 1.694 g (77%) Anal. Calcd. for (found) C$_{18}$F$_{15}$O$_3$Al: C, 37.52; (37.34). $^{19}$F NMR (282 MHz, DMSO-d$_6$): −161.2, −162.1, −162.8 (ortho-F); −169.9 (meta-F); 179.0 (para-F). $^{13}$C NMR (75 MHz, DMSO-d$_6$): 143.0, 142.4, 139.2, 136.0, 132.8, 129.7 (CF). The molecular structure of the compound is shown in FIG. 1.

Example 2

Preparation of [(Et$_2$O)$_2$H][Al(OC$_6$F$_5$)$_4$]

At 0° C. a solution of perfluorophenol (7.5 ml, 15 mmol) in 20 ml of diethylether was treated dropwise with 1.9M triethylaluminium solution (1.7 ml, 3.2 mmol). After 2 hours at room temperature the solvent was removed under vacuum and the product washed twice with petroleum spirits to give a white powder. Yield: 1.641 g (56%). Anal. Calc. for (found) C$_{32}$H$_{21}$O$_6$F$_{20}$Al: C, 42.31 (42.28); H, 2.33 (2.47). $^1$H NMR (300 MHz, CDCl$_3$): 5.60 (br, 1H, H(OEt$_2$)); 4.39 (q, J=7 Hz, 8H, OCH$_2$CH$_3$); 1.55 (t, J=7 Hz, 12H, OCH$_2$CH$_3$). $^{19}$F NMR (282 MHz, CDCl$_3$): −163.7 (d, J=22 Hz, ortho-F); −165.8 (t, J=22 Hz, meta-F); −171.1 (t, J=22 Hz, para-F). $^{13}$C NMR (75 MHz, CDCl$_3$): 142.0, 140.0, 138.8, 136.6 (CF); 71.9 (OCH$_2$); 13.9 (OCH$_2$C$_3$).

Example 3

Preparation of (Et$_2$O)Al{OCH(C$_6$F$_5$)$_2$}$_3$

At 0° C. a solution of (C$_6$F$_5$)$_2$C(H)OH (5.79 g, 15.9 mmol) in 15 ml of diethylether was treated dropwise with 1.9M AlEt$_3$. The addition of AlEt$_3$ was continued portionwise until the starting alcohol was completely consumed by NMR analysis. The solvent was then removed under vacuum, the residue taken up in diethylether, and the solvent removed again to yield a white powder. Yield: 5.743 g (91%). Anal. Calcd. for C$_{43}$H$_{13}$O$_4$F$_{30}$ (found): C, 43.38 (44.14); H, 1.10 (1.50). $^1$H NMR (300 MHz, CDCl$_3$): 6.65 (s, 3H, OCH); 4.18 (q, J=7 Hz, 4H, OCH$_2$CH$_3$); 1.32 (t, J=7 Hz, 6H, OCH$_2$CH$_3$). $^{19}$F NMR (282 MHz, CDCl$_3$): −144.5 (ortho-F); −155.2 (meta-F); −162.6 (para-F). $^{13}$C NMR (75 MHz, CDCl$_3$): 146.5, 143.2, 139.6, 136.2 (CF); 116.8 (ipso-C); 69.6 (OCH$_2$CH$_3$); 61.7 (OCH); 13.3 (OCH$_2$CH$_3$). The molecular structure of the compound is shown in FIG. 2.

Example 4

Preparation of (Et$_2$O)Al{OC(CF$_3$)$_3$}$_3$

A solution of 4 ml (29 mmol) of perfluoro-tert-butanol in 10 ml of diethylether was cooled to 0° C. and treated with a 1.9M solution of triethylaluminium (3 ml, 5.7 mmol). After stirring overnight the solution was heated to 65° C. for a further day. After cooling the solvent was removed under vacuum to give fine needles of colorless product. Yield: 4.383 g (95%). $^1$H NMR (300 MHz, CDCl$_3$): 4.34 (q, J=7 Hz, 4H, OCH$_2$CH$_3$); 1.43 (t, J=7 Hz, 6H, OCH$_2$CH$_3$). $^{19}$F NMR (282 MHz, CDCl$_3$): −75.9 (CF$_3$). The molecular structure of this compound is shown in FIG. 3.

Example 5

Ethylene Oligomerisation with Al(OC$_6$F$_5$)$_3$ Activator

A 300 ml stainless steel reactor equipped with mechanical stirring was heated to 120° C. and purged with ethylene.

Toluene (80 ml) was added, saturated with ethylene, and the reactor brought to 45° C. $CrCl_3(thf)_3$ (30 μmol) and $Ph_2PN$($^i$Pr)$PPh_2$ (30 μmol) were added to a Schlenk flask under nitrogen and dissolved in 20 ml of toluene. To this solution was added 3 mmol of $AlEt_3$ (100 equivalents relative to Cr), and the resulting mixture was added to the reactor followed by 40 μmol $Al(OC_6F_5)_3$. The reactor was immediately charged with 40 bar of ethylene and the pressure kept constant throughout the reaction by the continuous addition of ethylene. After 30 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 4.124 g. The product distribution is shown in Table 1.

Example 6

Ethylene Oligomerisation with $Al(OC_6F_5)_3$ Activator

The same procedure as for example 5 was followed with the exception that 9 mmol of $AlEt_3$ was employed (300 equivalents relative to Cr). The total product mass was 3.655 g. The product distribution is shown in Table 1.

Example 7

Ethylene Oligomerisation with $Al(OC_6F_5)_3$ Activator

The same procedure as for example 5 was followed with the exception that 3 mmol of triisobutylaluminium (TIBAL, 100 equivalents relative to Cr) was employed in place of $AlEt_3$. The total product mass was 1.556 g. The product distribution is shown in Table 1.

Example 8

Ethylene Oligomerisation with $Al(OC_6F_5)_3$ Activator

The same procedure as for example 5 was followed with the exception that 0.9 mmol of $AlEt_3$ was employed (30 equivalents relative to Cr). The total product mass was 9.067 g. The product distribution is shown in Table 1.

Example 9

Ethylene Oligomerisation with Perfluorophenol (In-Situ Activator)

$CrCl_3(thf)_3$ (30 μmol) and $Ph_2PN$($^i$Pr)$PPh_2$ (30 μmol) were added to a Schlenk flask under nitrogen and dissolved in 20 ml of toluene. This was treated with 90 μmol of $C_6F_5OH$ followed by 0.9 mmol (30 equivalents) of $AlEt_3$. The resulting solution was immediately added to the reactor (reactor conditions as detailed in example 5), and charged with 40 bar ethylene. After 30 minutes the contents were worked up as detailed in example 5. The total product mass was 5.319 g. The product distribution is shown in Table 1.

Example 10

Comparative Example of Ethylene Oligomerisation without Phosphine Ligand

The same procedure as in example 9 was followed with the exception that $Ph_2PN$($^i$Pr)$PPh_2$ was omitted. The total product mass was 5.788 g. The product distribution is shown in Table 1.

Example 11

Ethylene Oligomerisation with $[(Et_2O)_2H][Al(OC_6F_5)_4]$ Activator

The procedure of example 5 was followed with 10 μmol $CrCl_3(thf)_3$, 12 μmol $Ph_2PN$($^i$Pr)$PPh_2$, 1 mmol $AlEt_3$ (100 equivalents), and 15 μmol of $[(Et_2O)_2H][Al(OC_6F_5)_4]$. The total product mass was 0.873 g. The product distribution is shown in Table 1.

Example 12

Ethylene Oligomerisation with $(Et_2O)Al\{OC(CF_3)_3\}_3$ Activator

The procedure of example 5 was followed with 20 μmol $CrCl_3(thf)_3$, 20 μmol $Ph_2PN$($^i$Pr)$PPh_2$, 2 mmol $AlEt_3$ (100 equivalents), and 35 μmol of $(Et_2O)Al[OC(CF_3)_3]_3$. The total product mass was 4.26 g. The product distribution is shown in Table 1.

Example 13

Ethylene Oligomerisation with $[Ph_3C][Al\{OC(CF_3)_3\}_4]$ Activator

A 300 ml stainless steel reactor equipped with mechanical stirring was heated to 120° C. and purged with ethylene. Methylcyclohexane (80 ml) was added, saturated with ethylene, and the reactor brought to 65° C. Methylcyclohexane solutions of $Cr(acac)_3$ (10 ml of 10 μmM, 10 μmol) and $Ph_2PN$($^i$Pr)$PPh_2$ (5 ml of 2.5 mM, 12.5 μmol) were added to a Schlenk flask under nitrogen and treated with 1.0 mmol of $AlEt_3$ (100 equivalents relative to Cr). The resulting solution was added to the reactor followed by 15 mol of $[Ph_3C][Al\{OC(CF_3)_3\}_4]$. The reactor was immediately charged with 40 bar of ethylene and the pressure kept constant throughout the reaction by the continuous addition of ethylene. After 60 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 25.36 g. The product distribution is shown in Table 1.

Example 14

Ethylene Oligomerisation with $[Ph_3C][Al\{OC(CF_3)_3\}_4]$ Activator

The procedure of example 5 was followed with 30 μmol $CrCl_3(thf)_3$, 30 μmol $Ph_2PN$($^i$Pr)$PPh_2$, 0.9 mmol $AlEt_3$ (30 equivalents), and 40 µmol of [Ph$_3$C][Al{OC(CF$_3$)$_3$}$_4$]. The reaction was continued for 1 hour. The total mass of product was 41.98 g. The product distribution is shown in Table 1.

Example 15

Ethylene Oligomerisation with [Ph$_3$C][Al{OC(CF$_3$)$_3$}$_4$] Activator

The same procedure as in example 14 was followed with the exception that 3 mmol of AlEt$_3$ (100 equivalents) was employed. The total mass of product was 52.62 g. The product distribution is shown in Table 1.

Example 16

Ethylene Oligomerisation with [Ph$_3$C][Al{OC(CF$_3$)$_3$}$_4$] Activator

The procedure of example 5 was followed with 10 µmol CrCl$_3$(thf)$_3$, 12 µmol Ph$_2$PN($^i$Pr)PPh$_2$, 6 mmol AlEt$_3$ (600 equivalents), and 12 µmol of [Ph$_3$C][Al{OC(CF$_3$)$_3$}$_4$]. The total mass of product was 0.748 g. The product distribution is shown in Table 1.

Example 17

Ethylene Oligomerisation with [Ph$_3$C][Al{OC(CF$_3$)$_3$}$_4$] Activator

The procedure of example 5 was followed with 10 µmol CrCl$_3$(thf)$_3$, 12 µmol Ph$_2$PN($^i$Pr)PPh$_2$, 3 mmol AlEt$_3$ (300 equivalents), and 15 µmol of [Ph$_3$C][Al{OC(CF$_3$)$_3$}$_4$]. The reaction was continued for 1 hour. The total mass of product was 29.77 g. The product distribution is shown in Table 1.

Example 18

Ethylene Oligomerisation with [Ph$_3$C][Al{OC(CF$_3$)$_3$}$_4$] Activator

The same procedure as in example 17 was followed with the exception that 1 mmol of AlEt$_3$ (100 equivalents) was employed. The total mass of product was 39.06 g. The product distribution is shown in Table 1.

Example 19

Ethylene Oligomerisation with [Ph$_3$C][Al{OC(CF$_3$)$_3$}$_4$] Activator

[CrCl$_3${Ph$_2$PN($^i$Pr)PPh$_2$}]$_2$ (10 µmol of Cr) was added to a Schlenk flask under nitrogen and suspended in 20 ml of toluene. This was treated with 1 mmol of AlEt$_3$ (100 equivalents) to give a homogeneous solution. [Ph$_3$C][Al{OC(CF$_3$)$_3$}$_4$] (10 µmol) was added to the reactor (reactor conditions as detailed in example 5), followed by the Cr/PNP/AlEt$_3$ solution, and the reactor was charged with 40 bar ethylene. After 30 minutes the contents were worked up as detailed in example 5. The total product mass was 8.65 g. The product distribution is shown in Table 1.

Example 20

Ethylene Oligomerisation with [Ph$_3$C][Al{OC(CF$_3$)$_3$}$_4$] Activator

A 300 ml stainless steel reactor equipped with mechanical stirring was heated to 120° C. and purged with ethylene. Methylcyclohexane (80 ml) was added, saturated with ethylene, and the reactor brought to 65° C. CrCl$_3$(thf)$_3$ (10 µmol) and Ph$_2$PN($^i$Pr)PPh$_2$ (12 µmol) were added to a Schlenk flask under nitrogen and dissolved in 5 ml of toluene. To this solution was added 1 mmol of AlEt$_3$ (100 equivalents relative to Cr). The resulting solution was added to the reactor followed by 15 µmol of [Ph$_3$C][Al{OC(CF$_3$)$_3$}$_4$]. The reactor was immediately charged with 40 bar of ethylene and the pressure kept constant throughout the reaction by the continuous addition of ethylene. After 60 minutes the ethylene supply was closed and the reactor cooled in an ice/water bath. Excess ethylene was bled and the reactor contents treated sequentially with 1000 µL of nonane (GC internal standard), MeOH and 10% HCl. A sample of the organic phase was taken for GC-FID analysis while the solid polyethylene produced was collected by filtration, washed with MeOH and dried at 100° C. The total product mass was 30.97 g. The product distribution is shown in Table 1.

Example 21

Comparative Example of Ethylene Oligomerisation with B(C$_6$F$_5$)$_3$ Activator A 300 ml stainless steel reactor equipped with mechanical stirring was heated to 120° C. and purged with ethylene. Toluene (80 ml) was added, saturated with ethylene, and the reactor brought to 45° C. CrCl$_3$(thf)$_3$ (20 µmol) and Ph$_2$PN($^i$Pr)PPh$_2$ (20 µmol) were added to a Schlenk flask under nitrogen and dissolved in 20 ml of toluene. To this solution was added 3 mmol of AlEt$_3$ (100 equivalents relative to Cr), and the resulting mixture was added to the reactor followed by 30 µmol B(C$_6$F$_5$)$_3$. The reactor was immediately charged with 50 bar of ethylene and the pressure kept constant throughout the reaction by the continuous addition of ethylene. After 30 minutes the ethylene supply was closed and the reactor cooled in an ice/water bath. Excess ethylene was bled and the reactor contents treated sequentially with 1000 µL of nonane (GC internal standard), MeOH and 10% HCl. A sample of the organic phase was taken for GC-FID analysis while the solid polyethylene produced was collected by filtration, washed with MeOH and dried at 100° C. The total product mass was 0.611 g. The product distribution is shown in Table 1.

Example 22

Comparative Ethylene Oligomerisation with MMAO-3A Activator

The same procedure as in example 20 was followed with the exception that 1 mmol of MMAO-3A was employed as an activator in the place of AlEt$_3$ and [Ph$_3$C][Al{OC(CF$_3$)$_3$}$_4$], and 40 bar of ethylene was fed. The total mass of product was 13.49 g. The product distribution is shown in Table 1.

Example 23

Comparative Ethylene Oligomerisation with MMAO-3A Activator

The same procedure as in example 20 was followed with the exception that 4.0 mmol of MMAO-3A was employed as an activator in the place of AlEt$_3$ and [Ph$_3$C][Al{OC(CF$_3$)$_3$}$_4$], and 30 bar of ethylene was fed. The total mass of product was 37.39 g. The product distribution is shown in Table 1.

Example 24

Preparation of Cr(CO)$_4$ Ph$_2$PN($^i$Pr)PPh$_2$

Cr(CO)$_6$ (1.54 g, 7.0 mmol) and Ph$_2$PN($^i$Pr)PPh$_2$ (2.99 g, 7.0 mmol) were dissolved in diglyme (60 ml) and heated to 170° C. for 2 hours during which time the solution turned yellow. The solution was cooled and methanol (40 ml) was added which precipitated a yellow solid. The solution was filtered and the solid was washed with MeOH and dried in vacuo. Yield=2.65 g (64%). Anal. Calcd. for C$_{31}$H$_{27}$CrNO$_4$P$_2$ (found): C, 62.95 (62.94); H, 4.60 (4.55); N, 2.37 (2.31).

Example 25

Preparation of [Cr(CO)$_4$Ph$_2$PN($^i$Pr)PPh$_2$][Al{OC(CF$_3$)$_3$}$_4$]

A dichloromethane (5 ml) solution of Ag[Al{OC(CF$_3$)$_3$}$_4$] (147 mg, 0.13 mmol) was added to a dichloromethane (5 ml) solution of Cr(CO)$_4$Ph$_2$PN($^i$Pr)PPh$_2$ (75 mg, 0.13 mmol). The solution immediately darkened and after stirring for 1 hour the solution was filtered and the solid washed with dichloromethane (2×5 ml). The solvent was removed in vacuo from the combined organic fractions to leave a blue solid. Yield=150 mg (74%). Anal. Calcd. for C$_{47}$H$_{27}$AlCrF$_{36}$NO$_8$P$_2$ (found): C, 36.22 (36.19); H, 1.75 (1.73); N, 0.90 (0.87).

Example 26

Ethylene Oligomerisation with [Cr(CO)$_4$Ph$_2$PN($^i$Pr)PPh$_2$][Al{OC(CF$_3$)$_3$}$_4$]

A 300 ml glass Buchi reactor was heated to 120° C. and evacuated and back filled with nitrogen 3 times. Methylcyclohexane (40 ml) was added followed by a toluene (10 ml) solution of [Cr(CO)$_4$Ph$_2$PN($^i$Pr)PPh$_2$][Al{OC(CF$_3$)$_3$}$_4$] (31 mg, 20 μmol). To the reactor AlEt$_3$ (2 mmol, 100 equivalents relative to Cr) was added and the reactor was immediately charged with ethylene to a pressure of 8 bar. The solution was then irradiated with UV light from a High Pressure 100 Watt Mercury Vapor Short Arc lamp with a total intensity of 13 Wcm$^{-1}$ for 10 minutes. The ethylene was slowly vented to a pressure of approximately 0.5 bar and the solution was then transferred to a 300 ml stainless steel reactor equipped with mechanical stirring which had been heated to 120° C., purged with ethylene, methylcyclohexane (50 ml) added and the reactor temperature brought to 60° C. The reactor was immediately charged with 40 bar of ethylene and the pressure kept constant throughout the reaction by the continuous addition of ethylene. After 45 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 38.97 g. The product distribution is shown in Table 1.

Example 27

Ethylene Oligomerisation with [Cr(CO)$_4$Ph$_2$PN($^i$Pr)PPh$_2$][Al{OC(CF$_3$)$_3$}$_4$]

A 300 ml stainless steel reactor equipped with mechanical stirring was heated to 120° C. and purged with ethylene. Methylcyclohexane (90 ml) was added and the reactor brought to 60° C. [Cr(CO)$_4$Ph$_2$PN($^i$Pr)PPh$_2$][Al{OC(CF$_3$)$_3$}$_4$] (8 mg, 5 μmol) was dissolved in toluene (10 cm$^3$) and Et$_3$Al (2 mmol, 400 equivalents relative to Cr) was added. The resultant solution was added to the reactor and the reactor was immediately charged with 40 bar of ethylene and the pressure kept constant throughout the reaction by the continuous addition of ethylene. After 60 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 10.74 g. The product distribution is shown in Table 1.

Example 28

Ethylene Oligomerisation with [Cr(CO)$_4$Ph$_2$PN($^i$Pr)PPh$_2$][Al{OC(CF$_3$)$_3$}$_4$]

A 300 ml stainless steel reactor equipped with mechanical stirring was heated to 120° C. and purged with ethylene. Methylcyclohexane (90 ml) was added and the reactor brought to 60° C. Et$_3$Al (0.5 mmol, 100 equivalents relative to Cr) followed by tri-iso-butylaluminium (1.5 mmol, 300 equivalents relative to Cr) was added. [Cr(CO)$_4$Ph$_2$PN($^i$Pr)PPh$_2$][Al{OC(CF$_3$)$_3$}$_4$] (8 mg, 5 μmol) was dissolved in toluene (10 cm$^3$) and the resultant solution was added to the reactor. The reactor was immediately charged with 40 bar of ethylene and the pressure kept constant throughout the reaction by the continuous addition of ethylene. After 60 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 17.47 g. The product distribution is shown in Table 1.

Example 29

Ethylene Oligomerisation with [Ph$_3$C][Al{OC(CF$_3$)$_3$}$_4$] Activator

The same procedure as in example 17 was followed with the exception that 1 mmol of AlEt$_3$ (100 equivalents) was employed and the ethylene source was Linde 4.5. The total mass of product was 65.31 g. The product distribution is shown in Table 1.

Example 30

Ethylene Oligomerisation with [Cr(CO)$_4$Ph$_2$PN($^i$Pr)PPh$_2$][Al{OC(CF$_3$)$_3$}$_4$]

The same procedure as in example 27 was followed with the exception that 1 mmol of AlEt$_3$ (100 equivalents) was employed and the ethylene source was Linde 4.5. The total mass of product was 32.8 g. The product distribution is shown in Table 1.

Example 31

Ethylene Oligomerisation with [Cr(CO)$_4$Ph$_2$PN($^i$Pr)PPh$_2$][Al{OC(CF$_3$)$_3$}$_4$]

The same procedure as in example 27 was followed with the exception that 1 mmol of AlEt$_3$ (200 equivalents) was employed and the ethylene source was Linde 4.5. The total mass of product was 36.4 g. The product distribution is shown in Table 1.

Example 32

Ethylene Oligomerisation with [Ph$_3$C][Ta(OC$_6$F$_5$)$_6$] Activator

The procedure of example 5 was followed with 10 mmol CrCl$_3$(thf)$_3$, 12 µmol Ph$_2$PN($^i$Pr)PPh$_2$, 1 mmol AlEt$_3$ (100 equivalents), and 20 µmol of [Ph$_3$C][Ta(OC$_6$F$_5$)$_6$]. The total product mass was 0.691 g. The product distribution is shown in Table 1.

Example 33

Ethylene Oligomerisation with [Ph$_3$C][AlF{OC(CF$_3$)$_3$}$_3$] Activator

The procedure of example 5 was followed with 10 mol CrCl$_3$(thf)$_3$, 12 µmol Ph$_2$PN($^i$Pr)PPh$_2$, 1 mmol AlEt$_3$ (100 equivalents), and 15 µmol of [Ph$_3$C][AlF{OC(CF$_3$)$_3$}$_3$]. The total product mass was 1.187 g. The product distribution is shown in Table 1.

Example 34

Ethylene Oligomerisation with [Ph$_3$C][Al$_2$F{OC(CF$_3$)$_3$}$_6$] Activator The procedure of example 5 was followed with 10 µmol CrCl$_3$(thf)$_3$, 12 µmol Ph$_2$PN($^i$Pr)PPh$_2$, 1 mmol AlEt$_3$ (100 equivalents), and 10 µmol of [Ph$_3$C][Al$_2$F{OC(CF$_3$)$_3$}$_6$]. The total product mass was 3.60 g. The product distribution is shown in Table 1, while the ratio of C$_8$/C$_6$ is shown in FIG. 4.

Example 35

Ethylene Oligomerisation with [Ph$_3$C][Al$_2$F{OC(CF$_3$)$_3$}$_6$] Activator The procedure of example 5 was followed with 10 µmol CrCl$_3$(thf)$_3$, 12 µmol Ph$_2$PN($^i$Pr)PPh$_2$, 1 mmol AlEt$_3$ (100 equivalents), and 15 µmol of [Ph$_3$C][Al$_2$F{OC(CF$_3$)$_3$}$_6$]. The total product mass was 6.66 g. The product distribution is shown in Table 1, while the ratio of C$_8$/C$_6$ is shown in FIG. 4.

Example 36

Ethylene Oligomerisation with [Ph$_3$C][Al$_2$F{OC(CF$_3$)$_3$}$_6$] Activator The procedure of example 5 was followed with 10 µmol CrCl$_3$(thf)$_3$, 12 µmol Ph$_2$PN($^i$Pr)PPh$_2$, 1 mmol AlEt$_3$ (100 equivalents), and 20 µmol of [Ph$_3$C][Al$_2$F{OC(CF$_3$)$_3$}$_6$]. The total product mass was 7.14 g. The product distribution is shown in Table 1, while the ratio of C$_8$/C$_6$ is shown in FIG. 4.

Example 37

Ethylene Oligomerisation with [Ph$_3$C][Al$_2$F{OC(CF$_3$)$_3$}$_6$] Activator The procedure of example 5 was followed with 10 µmol CrCl$_3$(thf)$_3$, 12 µmol Ph$_2$PN($^i$Pr)PPh$_2$, 1 mmol AlEt$_3$ (100 equivalents), and 30 µmol of [Ph$_3$C][Al$_2$F{OC(CF$_3$)$_3$}$_6$]. The total product mass was 27.62 g. The product distribution is shown in Table 1, while the ratio of C$_8$/C$_6$ is shown in FIG. 4.

TABLE 1

Product distributions obtained in examples 5-19.

| Example | Productivity g/gCr | % PE | % C$_6$ | 1-C$_6$ | % C$_8$ | 1-C$_8$ |
|---|---|---|---|---|---|---|
| 5 | 2640 | 3.1 | 85.1 | 96.9 | 6.1 | 85.2 |
| 6 | 2340 | 2.3 | 89.9 | 95.6 | 4.7 | 74.4 |
| 7 | 997 | 6.4 | 86.0 | 97.8 | 4.0 | 96.8 |
| 8 | 5810 | 8.2 | 85.2 | 98.5 | 3.9 | 94.6 |
| 9 | 3410 | 16.0 | 78.3 | 97.9 | 1.8 | 84.4 |
| 10 | 3710 | 95.0 | 1.5 | 60.7 | 0.9 | 100 |
| 11 | 1680 | 12.6 | 63.9 | 95.0 | 23.5 | 97.6 |
| 12 | 4100 | 1.0 | 87.0 | 97.0 | 6.0 | 88.5 |
| 13 | 48770 | 3.6 | 24.7 | 82.4 | 64.9 | 99.1 |
| 14 | 26910 | 7.0 | 15.3 | 66.7 | 69.9 | 98.8 |
| 15 | 33730 | 0.7 | 16.2 | 66.9 | 72.9 | 98.6 |
| 16 | 1440 | 3.3 | 28.2 | 66.3 | 60.1 | 96.7 |
| 17 | 57250 | 1.3 | 16.9 | 66.3 | 72.7 | 98.0 |
| 18 | 75120 | 4.6 | 16.0 | 69.6 | 68.8 | 98.9 |
| 19 | 16630 | 8.5 | 13.6 | 66.1 | 64.8 | 98.9 |
| 20 | 59560 | 0.6 | 25.0 | 82.5 | 66.6 | 99.2 |
| 21 | 587 | 25.2 | 21.4 | 73.3 | 47.6 | 96.9 |
| 22 | 25940 | 33.9 | 18.2 | 86.6 | 45.8 | 99.2 |
| 23 | 71 860 | 0.20 | 27.7 | 88.9 | 64.2 | 99.4 |
| 26 | 37492 | 0.8 | 22.5 | 78.9 | 68.9 | 98.9 |
| 27 | 41305 | 0.3 | 23.2 | 75.8 | 74.2 | 99.4 |
| 28 | 67240 | 0.8 | 21.7 | 76.5 | 72.7 | 99.0 |
| 29 | 125600 | 0.41 | 16.3 | 68.9 | 72.2 | 99.0 |
| 30 | 126320 | 0.23 | 21.4 | 78.1 | 70.7 | 99.0 |
| 31 | 139832 | 1.1 | 21.4 | 78.8 | 72.4 | 99.0 |
| 32 | 1330 | 13.7 | 46.6 | 89.7 | 39.6 | 98.5 |
| 33 | 2280 | 33.3 | 34.6 | 80.8 | 32.1 | 87.7 |
| 34 | 6925 | 10.0 | 57.8 | 94.7 | 30.3 | 95.4 |
| 35 | 12810 | 21.6 | 44.0 | 95.9 | 25.5 | 98.2 |
| 36 | 13730 | 7.9 | 27.9 | 85.9 | 56.0 | 99.2 |
| 37 | 53120 | 6.5 | 18.6 | 76.3 | 68.2 | 99.4 |

Percentages are all mass %. 1-C$_6$ and 1-C$_8$ refer to mass % selectivity within the total C$_6$ and C$_8$ fractions respectively.

Example 38

Ethylene Oligomerisation with [(EtHex$_3$TAC)CrCl$_3$], Et$_3$Al Co-Activator and [Ph$_3$C][Al{OC(CF$_3$)$_3$}$_4$] Activator A 300 mL stainless steel reactor equipped with mechanical stirring was heated to 130° C. under vacuum for 1 hour. After cooling under vacuum and back-filling with Ar, [Ph$_3$C][Al{OC(CF$_3$)$_3$}$_4$] (30 µmol) and [(EtHex$_3$TAC)CrCl$_3$] [that is {tris-N,N,N,-ethylhexyl}1,3,5-tiazocyclohexane] (20 µmol) were added to the reactor as a solution in toluene (100 mL) and the reactor brought to 40° C. Et$_3$Al (2.0 mmol, 100 equivalents relative to Cr) was then added to the reactor and the vessel immediately charged with 2 bar of ethylene (Linde 4.5 grade) and the pressure kept constant throughout the reaction by the continuous addition of ethylene. After 37 minutes the ethylene supply was closed and the reactor cooled in an ice/water bath. Excess ethylene was bled and the reactor contents treated sequentially with 1000 µL of nonane (GC internal standard), MeOH and 10% HCl. A sample of the organic phase was taken for GC-FID analysis while the solid polyethylene produced was collected by filtration, washed with MeOH and dried at 100° C. The total product mass was 13.870 g. The product distribution is shown in Table 2.

Example 39

Ethylene Oligomerisation with [(EtHex$_3$TAC)CrCl$_3$], Et$_3$Al Co-Activator and [Ph$_3$C][Al{OC(CF$_3$)$_3$}$_4$] Activator A 300 mL stainless steel reactor equipped with mechanical stirring was heated to 130° C. under vacuum for 1 hour. After cooling under vacuum and back-filling with Ar, [Ph$_3$C][Al{OC(CF$_3$)$_3$}$_4$] (30 μmol) and [(EtHex$_3$TAC)CrCl$_3$] (20 μmol) were added to the reactor as a solution in toluene (100 mL) and the reactor brought to 50° C. Et$_3$Al (2.0 mmol, 100 equivalents relative to Cr) was then added to the reactor and the vessel immediately charged with 5 bar of ethylene (Linde 4.5 grade) and the pressure kept constant throughout the reaction by the continuous addition of ethylene. After 17 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 12.203 g. The product distribution is shown in Table 2.

Example 40

Comparative Ethylene Oligomerisation with [(EtHex$_3$TAC)CrCl$_3$] and MAO Activator A 300 mL stainless steel reactor equipped with mechanical stirring was heated to 130° C. under vacuum for 1 hour. After cooling under vacuum and back-filling with Ar, toluene (90 mL) and MAO (4.0 mmol, 200 equivalents relative to Cr) was added to the reactor and the temperature maintained at 40° C. In a schlenk [(EtHex$_3$TAC)CrCl$_3$] (20 μmol) was dissolved in toluene (10 mL) and MAO (2.0 mmol, 100 equivalents relative to Cr) added. The resultant solution was added to the reactor and the vessel immediately charged with 2 bar of ethylene (Linde 4.5 grade) and the pressure kept constant throughout the reaction by the continuous addition of ethylene. After 36 minutes the ethylene supply was closed and the reactor cooled in an ice/water bath. Excess ethylene was bled and the reactor contents treated sequentially with 100 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 9.941 g. The product distribution is shown in Table 2.

Example 41

Comparative Ethylene Oligomerisation with [(EtHex$_3$TAC)CrCl$_3$] and MMAO Activator A 300 mL stainless steel reactor equipped with mechanical stirring was heated to 130° C. under vacuum for 1 hour. After cooling under vacuum and back-filling with Ar, toluene (90 mL) and MMAO (4.0 mmol, 200 equivalents relative to Cr) was added to the reactor and the temperature maintained at 40° C. In a schlenk [(EtHex$_3$TAC)CrCl$_3$] (20 μmol) was dissolved in toluene (10 mL) and MMAO (2.0 mmol, 100 equivalents relative to Cr) added. The resultant solution was added to the reactor and the vessel immediately charged with 5 bar of ethylene (Linde 4.5 grade) and the pressure kept constant throughout the reaction by the continuous addition of ethylene. After 36 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 38.286 g. The product distribution is shown in Table 2.

TABLE 2

Product distributions obtained in examples 38-41.

| Example | Productivity g/gCr | Activity g/gCr/hr/bar | % PE | % C$_6$ | 1-C$_6$ | % C$_8$ | 1-C$_8$ |
|---|---|---|---|---|---|---|---|
| 38 | 13345 | 10820 | 46.1 | 36.6 | 99.2 | 3.7 | 86.0 |
| 39 | 11742 | 8288 | 62.3 | 28.4 | 99.3 | 4.7 | 90.6 |
| 40 | 9565 | 7971 | 25.1 | 43.8 | 99.0 | 3.0 | 71.0 |
| 41 | 36838 | 3400 | 29.8 | 34.1 | 99.4 | 4.3 | 91.2 |

Percentages are all mass %. 1-C$_6$ and 1-C$_8$ refer to mass % selectivity within the total C$_6$ and C$_8$ fractions respectively.

Example 42

Ethylene Oligomerisation with [{(Decyl-S—CH$_2$CH$_2$)$_2$NH}CrCl$_3$], Et$_3$Al Co-Activator and [Ph$_3$C][Al{OC(CF$_3$)$_3$}$_4$] Activator A 300 mL stainless steel reactor equipped with mechanical stirring was heated to 130° C. under vacuum for 1 hour. After cooling under vacuum and back-filling with Ar, [Ph$_3$C][Al{OC(CF$_3$)$_3$}$_4$] (30 μmol) and [{(Decyl-S—CH$_2$CH$_2$)$_2$NH}CrCl$_3$] (20 μmol) were added to the reactor as a solution in toluene (100 mL) and the reactor brought to 85° C. Et$_3$Al (2.0 mmol, 100 equivalents relative to Cr) was then added to the reactor and the vessel immediately charged with 40 bar of ethylene (Linde 3.5 grade) and the pressure kept constant throughout the reaction by the continuous addition of ethylene. After 21 minutes the ethylene supply was closed and the reactor cooled in an ice/water bath. Excess ethylene was bled and the reactor contents treated sequentially with 1000 μL of nonane (GC internal standard), MeOH and 10% HCl. A sample of the organic phase was taken for GC-FID analysis while the solid polyethylene produced was collected by filtration, washed with MeOH and dried at 100° C. The total product mass was 4.317 g. The product distribution is shown in Table 3.

Example 43

Comparative Ethylene Oligomerisation with [{(Decyl-S—CH$_2$CH$_2$)$_2$NH}CrCl$_3$] and MAO Activator A 300 mL stainless steel reactor equipped with mechanical stirring was heated to 130° C. under vacuum for 1 hour. After cooling under vacuum and back-filling with Ar, [{(Decyl-S—CH$_2$CH$_2$)$_2$NH}CrCl$_3$] (44 μmol) was added to the reactor as a solution in toluene (100 mL) and the reactor brought to 100° C. MAO (29.9 mmol, 680 equivalents relative to Cr) was then added to the reactor and the vessel immediately charged with 40 bar of ethylene (Linde 3.5 grade) and the pressure kept constant throughout the reaction by the continuous addition of ethylene. After 30 minutes the ethylene supply was closed and the reactor cooled in an ice/water bath. Excess ethylene was bled and the reactor contents treated sequentially with 1000 μL of nonane (GC internal standard), MeOH and 10%

HCl. A sample of the organic phase was taken for GC-FID analysis while the solid polyethylene produced was collected by filtration, washed with MeOH and dried at 100° C. The product distribution is shown in Table 3.

TABLE 3

Product distributions obtained in examples 42-43.

| Example | Productivity g/gCr | Activity g/gCr/hr | % PE | % $C_6$ | 1-$C_6$ | % $C_8$ | 1-$C_8$ |
|---|---|---|---|---|---|---|---|
| 42 | 3865 | 11044 | 0.7 | 84.2 | 99.3 | 3.3 | 93.7 |
| 43 | 13950 | 27900 | 2.3 | 96.1 | 99.5 | — | — |

Percentages are all mass %. 1-$C_6$ and 1-$C_8$ refer to mass % selectivity within the total $C_6$ and $C_8$ fractions respectively.

Example 44

1-Hexene Trimerisation with [(EtHex$_3$TAC)CrCl$_3$], Et$_3$Al Co-Activator and [Ph$_3$C][Al{OC(CF$_3$)$_3$}$_4$] Activator A 250 mL round bottom flask was dried in vacuo, back-filled with dry N$_2$ and charged with [Ph$_3$C][Al{OC(CF$_3$)$_3$}$_4$] (0.0363 g, 30 μmol), [(EtHex$_3$TAC)CrCl$_3$] (0.0116 g, 20 μmol), 1-hexene (20 mL), nonane (1 mL, as GC standard) and toluene (20 mL). This solution was heated in an oil bath to 40° C. Once a steady temperature had been achieved a solution of AlEt$_3$ 1.9M in toluene (1.1 ml, 2 mmol, 100 equivalents relative to Cr) was added. Upon activation the brown/yellow solution became yellow over a few seconds. The solution was stirred at constant temperature for 2 hours. The reaction was quenched with methanol (2 ml) and water (2 ml). Samples (0.2 ml) were taken from the reaction solution just prior to activation and after quenching. These were added to DCM (1.5 ml) and analysed by GC-FID. The product distribution is shown in Table 4.

Example 45

Comparative 1-Hexene Trimerisation with [(EtHex$_3$TAC)CrCl$_3$] and MMAO Activator A 250 mL round bottom flask was dried in vacuo, back-filled with dry N$_2$ and charged with [(EtHex$_3$TAC)CrCl$_3$] (0.0116 g, 20 μmol), 1-hexene (20 mL), nonane (1 mL, as GC standard) and toluene (20 mL). This solution was heated in an oil bath to 40° C. Once a steady temperature had been achieved a solution of MMAO 1.9M in heptanes (3.2 ml, 6.0 mmol, 300 equivalents relative to Cr) was added. Upon activation the purple solution instantly became green. The solution was stirred at constant temperature for 2 hours. The reaction was quenched with methanol (2 ml) and water (2 ml). Samples (0.2 ml) were taken from the reaction solution just prior to activation and after quenching. These were added to DCM (1.5 ml) and analysed by GC-FID. The product distribution is shown in Table 4.

TABLE 4

Product distributions obtained in examples 44-45.

| Example | TON Mol 1-$C_6$/mol Cr | Activity Mol 1-$C_6$/mol Cr/hr | Selectivity to C18 fraction |
|---|---|---|---|
| 44 | 29.9 | 14.9 | >99% |
| 45 | 1199.2 | 599.6 | >99% |

The above detailed examples reveal several advantages that can be achieved through the use of the activators and co-activators disclosed herein. Firstly, it is found that ethylene oligomerisation with a combination of a Cr source, Ph$_2$PN ($^i$Pr)PPh$_2$, and an alkylaluminoxane such a MAO or MMAO normally furnishes an oligomeric mixture composed predominately of 1-hexene and 1-octene, in which the amount of 1-octene is greater than the amount of 1-hexene. This is illustrated in comparative example 23, and further examples can be found in WO 04/056479 as well as Bollmann et. al., J. Am. Chem. Soc., 126 (2004) 14712. Surprisingly however, examples 5-9 and 11-12 show that it is possible to produce an oligomer composed predominately of 1-hexene by replacing aluminoxane activators with the activators and co-activators disclosed herein. Furthermore, it can be concluded by considering all examples, and as shown in FIG. 4, that control over the ratio of 1-hexene to 1-octene can be achieved through the choice of activator employed, the amount of activator employed, or the relative ratio of activator to co-activator.

A second advantage that can be achieved is a reduction in the total amount of aluminium that can be used while still maintaining acceptable productivity and selectivity. Comparative example 22 shows that when the amount of MMAO-3A is reduced down to 100 equivalents relative to chromium, a lower productivity results and a large amount of polymer is formed. Comparison of example 22 with examples 15 and 18 shows that a higher productivity and lower polymer content can be achieved with similar total amounts of aluminium. As such, there is provided a means by which waste volumes can be reduced. Furthermore, the co-activators that can be used in the present invention, such as triethylaluminium, are generally substantially less expensive than aluminoxanes, and as such a lower activator cost is achievable for a given amount of oligomeric product.

Compared to the use of borane or borate activators, which also allow inexpensive co-activators such a triethylaluminium to be employed, the activators disclosed herein are capable or much improved productivity. This is illustrated in comparative example 21, and further examples can be found in IPCOM000031729D, which show that borane and borate activators lead to lower productivity for oligomer formation. Examples 14, 15, 17 and 18 show that greatly improved productivities can be achieved through the use of the activators disclosed herein.

Examples 26-28 illustrate that it is possible to use a system in which the source of transition metal, ligating compound, and activator are all constituents of a single chemical compound. Example 26 shows that such a system is also capable of producing acceptable productivity and low solids formation with reduced total amounts of aluminium.

Examples 29-30 compared to examples 18 and 27 respectively show that the productivity obtained from a particular catalyst system is dependent on the source of ethylene used.

Examples 38-39 further demonstrate the application of the activator to other catalyst systems, specifically those employing tridentate ligands. More specifically a facially capping tridentate ligand. It can be seen by reference to the comparative examples 40 and 41 that compared to MAO or MMAO activators a significant reduction in the amount of aluminium utilised is achieved. Simultaneously a catalyst is generated with a higher activity per bar ethene per gram Cr per hour. It should be noted that in comparative example 40 an ethene pressure of 5 bar (as opposed to 2 bar in examples 38 and 39) is required for the catalyst to function.

Examples 42 further demonstrates the application of the activator to other catalyst systems, specifically those employing tridentate ligands. More specifically a meridional-binding mode tridentate ligand. Example 43 shows a comparison with MMAO.

Examples 44 demonstrates the application of the activator in conjunction with catalyst systems for the oligomerisation of α-olefins. Specifically the trimerisation of 1-hexene. Example 45 is a comparative example with MMAO as activator.

The invention claimed is:

1. A process for producing an oligomeric product by the oligomerisation of at least one olefinic compound in the form of an olefin or a compound having a carbon to carbon double bond, comprising contacting the at least one olefinic compound with the combination of an oligomerisation catalyst and a catalyst activator, which catalyst activator is a salt containing an anion which includes a moiety of the formula

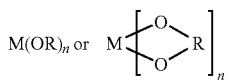

and wherein

M is selected from the group consisting of a group 3A atom;

n is 1 or a larger integer; and

R is a halogenated organic group, R being the same or different when n is larger than 1; and wherein the oligomerisation catalyst comprises the combination of i) a source of a transition metal; and ii) a ligating compound of the formula $(R^1)_m X^1 (Y) X^2 (R^2)_n$ wherein $X^1$ and $X^2$ are independently selected from the group consisting of N, P, As, Sb, Bi, 0, S, and Se;

Y is a linking group between $X^1$ and $X^2$;

m and n are independently 0, 1 or a larger integer; and $R^1$ and $R^2$ are independently hydrogen, a hydrocarbyl group or a heterohydrocarbyl group, and $R^1$ being the same or different when m>1, and $R^2$ being the same or different when n>1.

2. The process of claim 1 wherein the group 3A atom is selected from the group consisting of Al and B.

3. The process of claim 2 wherein the group 3A atom is Al.

4. The process of any one of claim 1 to 3 wherein R is a halogenated hydrocarbyl group, a halogenated heterohydrocarbyl group, a halogenated organyl group or a halogenated organoheteryl group.

5. The process of claim 4 wherein R is a halogenated hydrocarbyl group or a halogenated organyl group.

6. The process of claim 5 wherein all the hydrogen atoms of the organyl group or hydrocarbyl group are replaced with halogen atoms and all the halogen atoms are the same.

7. The process of claim 6 wherein all the halogen atoms are F.

8. The process of claim 1 wherein the activator is a salt containing the anion

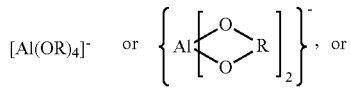

a compound having a moiety $Al(OR)_3$.

9. The process of claim 1 wherein the activator is selected from the group consisting of $Al(OC_6F_3)_3$; $X^+[Al\{OC(CF_3)_3\}_4]^-$; $X^+[Al(OC_6F_5)_4]^-$; $X^+[Al(C_6F_4O_2)_2]^-$; $X^+[AlF\{OC(CF_3)_2C(CF_3)_2O\}_2]$; $X^+[AlF\{OC(CF_3)_3\}_3]X^+[Al_2F\{OC(CF_3)_3\}_6]$; $(Z)Al\{OCH(C_6F_5)_2\}_3$; and $(Z)Al\{OC(CF_3)_3\}_3$, wherein $X^+$ is a cation selected from the group consisting of $Ph_3C^+$, $Me_2PhNH^+$ and $(Et_2O)_2H^+$; and wherein Z is a moiety bound to Al, which moiety Z is not an

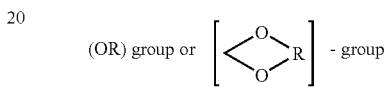

where R is a halogenated organic group.

10. The process of claim 1 further comprising a co-activator, wherein the co-activator is an organoaluminium compound and/or an organoboron compound.

11. The process of claim 10 wherein the co-activator is an organoaluminium compound of the formula $Al(R^9)_3$ ($R^9$ being the same or different), where each $R^9$ is independently an organyl group, a halogenated organyl group or a halide, with at least one of $R^9$ being an organyl group or a halogenated organyl group.

12. The process of claim 11 wherein the co-activator is selected from the group consisting of trimethyaluminium (TMA), triethylaluminium (TEA), tributylaluminium, triisobutylaluminium (TIBA) and tri-n-octylaluminium.

13. The process of claim 1 wherein the oligomerisation process comprises the trimerisation and/or tetramerisation of ethylene.

14. The process of claim 1 wherein the source of the transition metal of the oligomerisation catalyst is a source of Cr.

15. The process of claim 1 wherein the ligating compound of the oligomerisation catalyst is of the formula

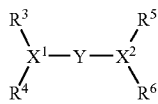

wherein $X^1$ and $X^2$ are independently selected from the group consisting of N, P, As, Sb and Bi; and $R^3$ to $R^6$ are each independently a hydrocarbyl group or a heterohydrocarbyl group.

16. The process of claim 15 wherein $X^1$ and $X^2$ are the same and both are P.

* * * * *

UNITED STATES PATENT AND TRADEMARK OFFICE
CERTIFICATE OF CORRECTION

PATENT NO.        : 8,134,038 B2
APPLICATION NO.   : 11/992740
DATED             : March 13, 2012
INVENTOR(S)       : David Shane McGuinness and Adam John Rucklidge It is certified that error appears in the above-identified patent and that said Letters Patent is hereby corrected as shown below:

Title page, item [57], line 3, "olefiπic" should read -- olefinic --.

Title page, item [57], line 15, "aligomerisation" should read -- oligomerisation --.

* Claim 9, col. 28, line 14, "$X^+[AlF\{OC(CF_3)_2C(CF_3)_2O\}_2]$;" should read -- $X^+[Al\{OC(CF_3)_2C(CF_3)_2O\}_2]$; --.

Signed and Sealed this
Thirtieth Day of October, 2012

David J. Kappos
*Director of the United States Patent and Trademark Office*